(12) United States Patent
Seibel et al.

(10) Patent No.: US 12,241,901 B2
(45) Date of Patent: Mar. 4, 2025

(54) SYSTEMS AND METHODS FOR ACCURATE OPTICAL PH SENSING OF BIOFILMS

(71) Applicant: University of Washington, Seattle, WA (US)

(72) Inventors: Eric J. Seibel, Seattle, WA (US); Leonard Y. Nelson, Seattle, WA (US); Manuja Sharma, Seattle, WA (US); Jasmine Graham, Seattle, WA (US)

(73) Assignee: The University of Washington, Seattle, WA (US)

( * ) Notice: Subject to any disclaimer, the term of this patent is extended or adjusted under 35 U.S.C. 154(b) by 1081 days.

(21) Appl. No.: 17/260,957

(22) PCT Filed: Jul. 19, 2019

(86) PCT No.: PCT/US2019/042665
§ 371 (c)(1),
(2) Date: Jan. 15, 2021

(87) PCT Pub. No.: WO2020/018946
PCT Pub. Date: Jan. 23, 2020

(65) Prior Publication Data
US 2021/0263051 A1 Aug. 26, 2021

Related U.S. Application Data

(60) Provisional application No. 62/700,873, filed on Jul. 19, 2018.

(51) Int. Cl.
*G01N 21/64* (2006.01)
*G01N 33/52* (2006.01)
*G01N 33/84* (2006.01)

(52) U.S. Cl.
CPC ............. *G01N 33/84* (2013.01); *G01N 21/64* (2013.01); *G01N 33/52* (2013.01)

(58) Field of Classification Search
CPC ......... G01N 21/64; G01N 33/52; G01N 33/84
See application file for complete search history.

(56) References Cited

U.S. PATENT DOCUMENTS

| | | | |
|---|---|---|---|
| 6,834,237 B2 | 12/2004 | Noergaard et al. | |
| 7,190,457 B2 | 3/2007 | Tabacco et al. | |
| 9,377,396 B2 | 6/2016 | Goldring et al. | |
| 2003/0212265 A1* | 11/2003 | Tsien | G01N 33/84 |
| | | | 435/325 |
| 2006/0275847 A1* | 12/2006 | Goodyer | G01N 21/6452 |
| | | | 435/25 |
| 2009/0035783 A1 | 2/2009 | Yang | |
| 2009/0124690 A1* | 5/2009 | Alberte | C07C 309/66 |
| | | | 560/61 |
| 2010/0291618 A1 | 11/2010 | Robinson et al. | |
| 2015/0241438 A1 | 8/2015 | Gee et al. | |
| 2016/0139158 A1* | 5/2016 | Dzubay | C09B 11/28 |
| | | | 546/37 |
| 2016/0223558 A1* | 8/2016 | Strongin | G01N 33/52 |

FOREIGN PATENT DOCUMENTS

WO 2018/081637 A1 5/2018

OTHER PUBLICATIONS

Zhang, Liang, et al. "Trimodal detection of early childhood caries using laser light scanning and fluorescence spectroscopy: clinical prototype." Journal of biomedical optics 18.11 (2013): 111412.
Han, Junyan, et al. "A ratiometric pH reporter for imaging protein-dye conjugates in living cells." Journal of the American Chemical Society 131.5 (2009): 1642-1643.
Kubista, M., et al., "Quantitative Spectral Analysis of Multicomponent Equilibria," Analytica Chimica Acta 302(1):121-125, Feb. 1995.
Sharma, M., et al., "Optical pH Measurement System Using a Single Fluorescent Dye for Assessing Susceptibility to Dental Caries," Journal of Biomedical Optics 24(1): 017001-1-017001-8, Jan. 2019.
Susuma, K., et al., "Purple-, Blue-, and Green-Emitting Multishell Alloyed Quantum Dots: Synthesis, Characterization, and Application for Ratiometric Extracellular pH Sensing," Chemistry of Materials 29(17): 7330-7344, Aug. 2017.
"TRITC Excitation Filter," Thorlabs Inc., Sep. 16, 2009, 1 page.
International Search Report and Written Opinion, mailed Oct. 3, 2019 issued in corresponding International Application No. PCT/US2019/042665, filed Jul. 19, 2019, 13 pages.
Wolf, G., et al., "Optical and Spectroscopic Methods for Biofilm Examination and Monitoring," Reviews in Environmental Science and Biotechnology 1:227-251, Sep. 2002.
Graham, J., et al., "Optical Measurement of Acidification of Human Dental Plaque in Vitro," Proceedings of SPIE (Society of Photo Optical Instrumentation Engineers) 10473, Lasers in Dentistry XXIV: 104730A-1-104730A10, Feb. 2018.

* cited by examiner

*Primary Examiner* — Randy Boyer
(74) *Attorney, Agent, or Firm* — Christensen O'Connor Johnson Kindness PLLC

(57) ABSTRACT

Systems and methods for accurate optical pH sensing of biofilms are disclosed. In one embodiment, a method of measuring an extracellular pH level using multiple wavelengths emitted by a fluorescent substance includes: exciting the fluorescent substance at an excitation wavelength; measuring a first fluorescence intensity at a first wavelength of a fluorescence emission; and measuring a second fluorescence intensity at a second wavelength of the fluorescence emission. The second wavelength is different from the first wavelength. The method also includes determining the extracellular pH level based on the first fluorescence intensity at the first wavelength and the second fluorescence intensity at the second wavelength.

18 Claims, 8 Drawing Sheets

SYSTEMS AND METHODS FOR ACCURATE OPTICAL PH SENSING OF BIOFILMS

CROSS REFERENCES TO RELATED APPLICATIONS

This application is a National Phase of International Application No. PCT/US2019/042665, filed Jul. 19, 2019, which claims the benefit of Provisional Application No. 62/700,873, filed Jul. 19, 2018, the entire disclosures of which are hereby incorporated herein by reference.

STATEMENT REGARDING FEDERALLY SPONSORED RESEARCH

This invention was made with government support under Grant No. 1631146, awarded by the National Science Foundation. The government has certain rights in the invention.

BACKGROUND

Each year an estimated 48 million Americans are stricken ill as the result of one food-borne pathogen or another—*Listeria, E. coli, Salmonella,* and even a number of stow-away viruses are among the culprits. But in many cases the victims don't know they've been infected. For those who go to a doctor or the hospital, the collective bill is substantial. A 2015 study by Ohio State University estimates the annual cost of medical treatment, lost productivity, and illness-related mortality at $55.5 billion.

Human consumption of bacterial contaminated food biofilms can lead to death and debilitating long term illness (e.g., kidney failure). Bacteria specific test methods are needed for early identification of bacterial contamination. Current testing is based on ATP bioluminescence which is not bacteria specific and may be insensitive to gram negative bacterial. Real time identification of pathogenic bacteria/biofilms is critical in many settings yet no bacterial specific methodology exists for rapid detection.

Biofilms are surface-associated, three-dimensional structures whose integrity depends upon an extracellular matrix of exopolysaccharide (EPS) produced by their constituent bacterial cells. The two most generalizable features of these biofilms are microcolonies, composed of cells surrounded by large amounts of exopolysaccharide (EPS), and water-filled channels, which have been hypothesized to promote the influx of nutrients and the efflux of waste products.

Biofilm formation occurs as a result of a sequence of events: adhesion of individual microbial cells to a surface, cell proliferation and aggregation into microcolonies, matrix production, and cell detachment. Initiation of biofilm formation is characterized by the interaction of bacterial cells with a surface and with each other. The biofilm matures through the production of extracellular matrix which is mainly composed of sticky polysaccharides (EPS) and proteins. Various pathogenic bacteria can attach to and grow on surfaces, thereby forming a "biofilm."

Biofilm formation is a major problem in food processing environment and in wounds, or on surgical instruments in a medical environment. Food processing environment, in which organic matter such as food scraps or food processing wastewater is abundant, can harbor microorganisms in biofilm; these microbes are a major source of cross-contamination.

Biofilms metabolize nutrients such as sugars and release acidic byproducts into their environment as evidenced by a localized pH drop. Reliable and quantitative non-contact methods for measuring acidity levels that are also biocompatible and food safe, are not currently available. For example, simple chemical test strips for acidity require intimate contact with surfaces and interpretation of the color shading scale is subject to human error.

Oral biofilms may be a medium that enables tooth decay or the caries process of acidification and enamel demineralization. Criteria for assessing an individual's susceptibility to caries are often associated with a well-known 1940's study by R. M. Stephan where the time dependent drop in the plaque pH is measured before and after administration of a sugar rinse. Test subjects were divided into groups ranging from caries-free to caries-active. The pre-rinse pH, denoted as the "resting-pH", and the recovery to near normal pH levels was significantly different for each group. The results of a more recent 1999 published study with many more test subjects exhibit the same trends as the earlier Stephan work, albeit with less difference in the minimum pH trough value between caries-free and caries-active subjects as shown in FIG. 1.

Figure 1:
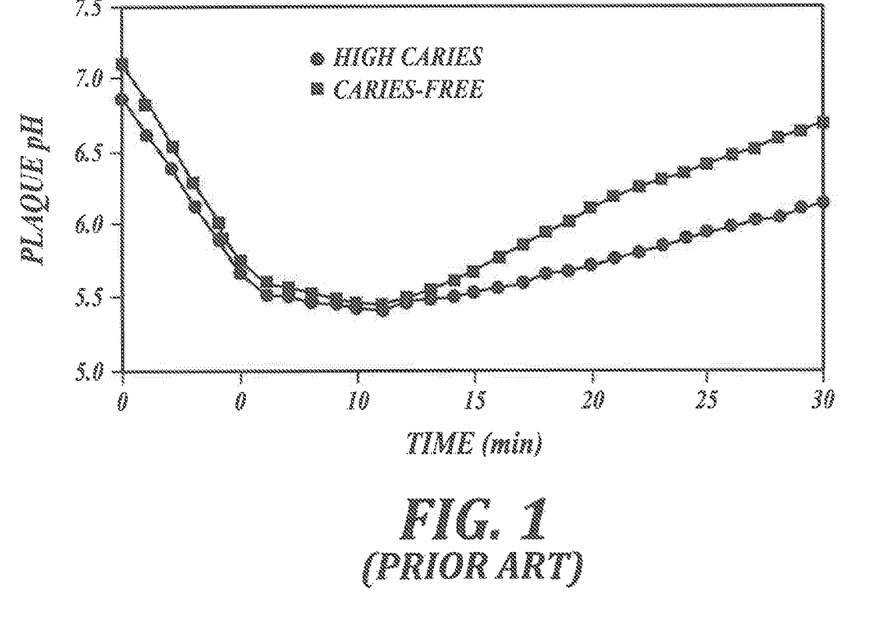
FIG. 1 is a graph of a plaque pH as a function of time in accordance with prior art.

FIG. 1 is a graph of a plaque pH as a function of time in accordance with prior art. The horizontal axis shows time after sugar was applied to a surface (e.g., teeth of a patient). Such a sucrose rinse accelerates bacterial metabolism leading to an increase in the production of acidic byproducts and facilitates measurements of the time-dependent drop in pH. The vertical axis shows the pH of the plaque on the surface measured with a small electronic probe. Square symbols correspond to a carries-free environment and circle symbols correspond to a high-carries environment.

FIG. 1 shows two distinguishing features of the time-dependent pH measurements. First, the caries-free group exhibits a faster pH rise to a higher value after the sugar rinse. The caries-active group has a much slower pH recovery that reaches a lower value than the caries-free group. Second, the average initial (resting) pH prior to the sugar rinse is measurably higher for the caries-free population. Hence, it is desirable to measure both the resting and recovery pH following a sugar rinse or simply the resting pH which can be done rapidly without the addition of sugar. In some situations, the pH values may be proxies for the amount of caries in patient's mouth. Therefore, there is a need to quantitatively measure the pH values before and shortly after the sugar rinse.

Quantitative pH measurements have historically depended on electronic sensing devices that rely on direct contact with the medium of interest. These instruments contain a fragile probe and also require direct contact with the oral biofilm covering the surface. Furthermore, these electronic sensing devices may become contaminated by having their surfaces coated with a biofilm that accumulates over time and require careful cleaning. For accurate assessment of the acidic state of the biofilm, it is necessary to measure the pH within the microscopic biofilm environment which includes live and dead colonies of bacteria of various species and their extracellular structures, bathing solution, and food/nutrients. Detailed confocal microscopy studies have shown that a pH gradient exists in the biofilm that reflects the depletion of nutrients and oxygen at the base of the biofilm. Hence the acidity is much higher at the interface of the biofilm and enamel surface. Therefore, a surface contact probe will not accurately measure the actual pH at the enamel surface.

Figure 2:
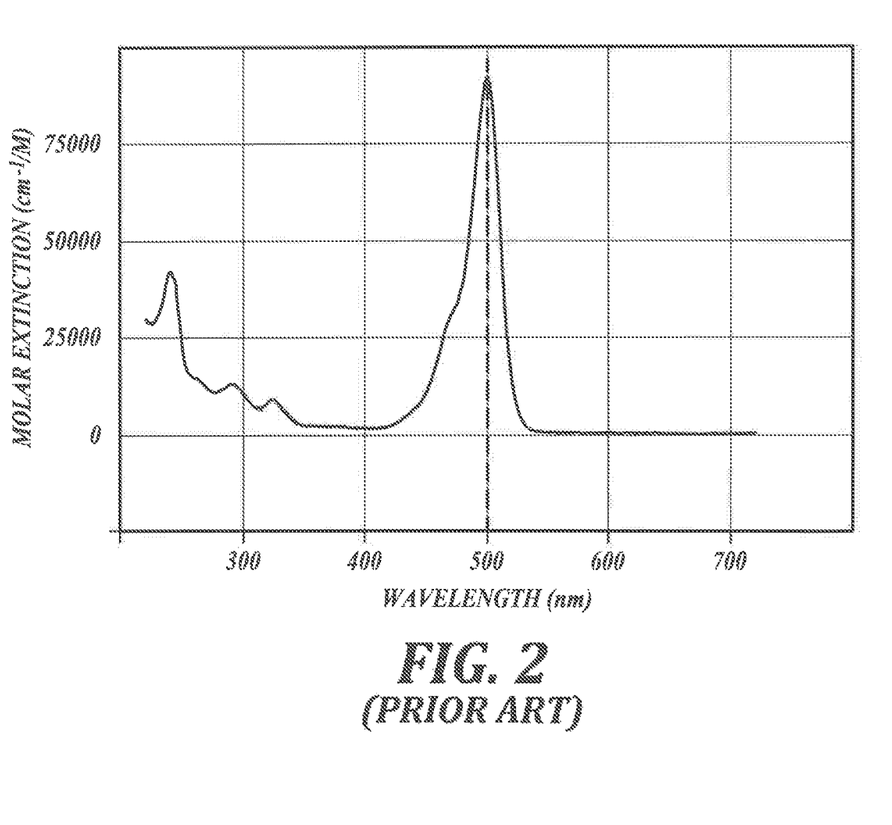
FIG. 2 is a graph of the fluorescein absorption spectral profile as a function of wavelength in accordance with prior art.

FIG. 2 is a graph of the absorption spectra for fluorescein as a function of wavelength in accordance with prior art. The horizontal axis shows the wavelength of the incoming light in nanometers (nm). The vertical axis shows the absorption.

The illustrated fluorescent substance, fluorescein, has a peak absorption of light at about 490 nm. Fluorescein emits a portion of this absorbed light, but at longer wavelengths, as shown in FIG. 3 below.

Figure 3:
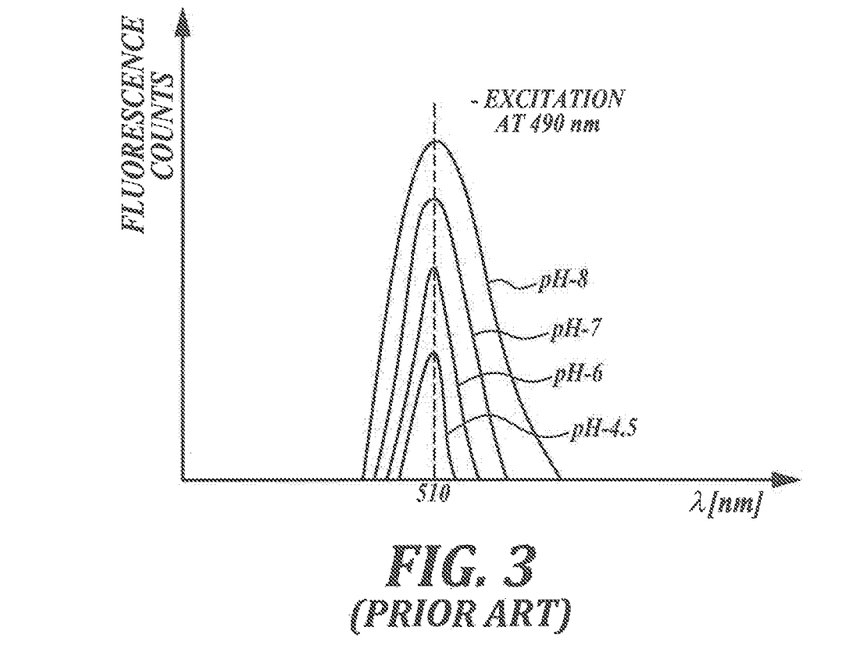
FIG. 3 is a graph of fluorescein counts as a function of wavelength in accordance with prior art.

FIG. 3 is a graph of fluorescence intensity as a function of wavelength in accordance with prior art. The horizontal axis shows wavelength of the emitted light in nanometers (nm). The vertical axis shows the intensity of the fluorescence (emitted light) in counts. The fluorescence was based on the excitation light at 490 nm.

The graph shows a family of curves for different pH values. The illustrated range of pH values spans from "pH-8" corresponding to pH of 8 to "pH-4.5" corresponding to pH of 4.5. Such a range of pH values generally spans and exceeds the range of pH values in a patient's mouth. As the pH decreases from the maximum illustrated value pH-8 to the minimum illustrated value of pH-4.5, the amount of fluorescence (i.e., emitted light) also decreases. In operation, the fluorescence is measured at its peak intensity (typically, close to 510 nm for fluorescein), and the intensity of the measured fluorescence is correlated to the pH level.

However, such measurements of fluorescence intensity can be prone to error as a result of several factors including the stability of the excitation light source(s), light scattering, dye photobleaching, dye quenching, etc., making these intensity dependent measurements susceptible to changes in experimental conditions during the measurement. Accordingly, systems and methods are needed for improved measurements of pH level in a patient's mouth.

SUMMARY

This summary is provided to introduce a selection of concepts in a simplified form that are further described below in the Detailed Description. This summary is not intended to identify key features of the claimed subject matter.

Briefly, the inventive technology is directed to pH measurements that are based on fluorescence of fluorescein (or other fluorescent compounds). In some embodiments, the excitation (absorption) light is provided at one wavelength, while the fluorescence is measured at multiple wavelengths or two wavelengths or two relatively narrow wavebands. These fluorescence wavelengths are representative of the dianion and anion molecular variants (also referred to as the components or phases) of fluorescein. As the acidity level (i.e., the pH level) increases, the concentration of dianion increases, while the concentration of anion decreases. These two species have overlapping absorption and emission spectral characteristics.

In some embodiments of the inventive technology, the overlapping spectral emission of dianion and anion are unmixed using curve fitting (e.g., least square fitting) to determine the pH of the measured specimen. For example, at the pH value of 4, a fluorescein solution consists of predominantly anion species (A) and at the pH value of 9, the solution consists of predominantly dianion species (D), thus resulting in different spectral properties within the 450- to 650-nm range. In some embodiments, the spectral properties of these endmembers (pH 4 and 9) for pure anion and dianion species are linearly unmixed for unknown pH solutions in the 4.5 to 7 range to determine the unknown pH value, because solutions between pH 4.5 and 7 contain both dianion and anion species resulting in a fluorescent spectral profile that is a mixture of the individual emission profiles of anion and dianion.

In some embodiments, the excitation wavelength of 420 nm balances a relatively stronger dianion fluorescent emission against a relatively weaker anion fluorescent emission, therefore improving the performance of the unmixing algorithm. Unwanted noise contributions, such as background light and autofluorescence (AF) in the range of 450 to 650 nm, may be removed before determining the biofilm pH. Spectral unmixing of the normalized fluorescence spectral profiles of the dianion and anion components results in a pH measurement that relies on a single excitation wavelength, while still being relatively insensitive to changes in dye (e.g., fluorescence) concentration, excitation intensity, and photobleaching. In some embodiments, these measurements may be referred to as chemometric measurements or chemometric spectra isolation. Since an optical beam illuminates the fluorescein embedded in the biofilm, this method does not require contact between a physical probe and the biofilm.

In applying a pH sensitive optical dye molecule, such as sodium fluorescein (also referred to as a fluorescein) or a modification of chlorin e6 (a food additive), the microscopic pH environment of the biofilm can be assessed in a rapid and non-contact measurement technique. By virtue of its negative charge, fluorescein resides in the extracellular region of a bacteria or biofilm. It does not cross the cellular membrane and is regarded as an "exclusion" dye in microscopy. In some embodiments more than one dye molecule can be used, but typically only one dye needs to be pH sensitive in the range of 7 to 4 pH. If used, the second dye molecule can be a sub-species of the pH sensitive dye or a natural dye molecule in the biofilm. Some families of dye molecules are ultra-violet to visible to near infrared light fluorescence molecules, including derivatives of fluorescein and boron dipyrromethene (BODIPY). BODIPY may be modified to create properties in a biofilm described in the present disclosure. Other molecules are near-infrared dyes that change absorption properties with pH. The optical measurement of pH resulting from introduction of the modified dye or dyes to biofilm is robust to changes in illumination and detection of the optical signal and to changes in dye concentration in the biofilm and also chemical and physical (thickness) differences in the biofilm.

In some embodiments, a method of measuring an extracellular pH level using multiple wavelengths emitted by a fluorescent substance includes: exciting the fluorescent substance at an excitation wavelength; measuring a first fluorescence intensity at a first wavelength of a fluorescence emission; and measuring a second fluorescence intensity at a second wavelength of the fluorescence emission. The second wavelength is different from the first wavelength. The method also includes determining the extracellular pH level based on the first fluorescence intensity at the first wavelength and the second fluorescence intensity at the second wavelength.

In one aspect, the fluorescent substance is a fluorescein.

In another aspect, the method also includes calibrating the fluorescence emission of an anion component and a dianion component of the fluorescein. The calibration is performed by subtracting ambient emission from the anion component and the dianion component; and dividing the anion component and the dianion component by a peak spectral intensity to normalize the anion component and the dianion component.

In one aspect, the extracellular pH level is determined based on Equation 1 below:

Measured Spectrum=$A\_1$*(Anion Spectrum)+$A\_2$*(Dianion Spectrum)   (Eq. 1)

where: A1 and A2 are calibration constants, Dianion Spectrum is measured at the first wavelength, and Anion Spectrum is measured at the second wavelength.

In one aspect, the excitation wavelength is within a range of 404-430 nm.

In another aspect, the excitation wavelength is 420 nm.

In one aspect, the first fluorescence wavelength is within a range of 515 to 525 nm.

In one aspect, the second fluorescence wavelength is within a range of 545 to 555 nm.

In one aspect, the extracellular pH level is determined over a layer of bacteria developed on a tooth plaque.

In another aspect, the extracellular pH level is determined in drinking water.

In yet another aspect, the extracellular pH level is determined over a surface of a plant. The plant may be a vegetable plant.

In one embodiment, a system for measuring an extracellular pH level using multiple wavelengths emitted by a fluorescent substance includes: a source of light configured to emit excitation light toward a target biological surface that includes the fluorescent substance; a first wavelength filter configured to bandpass a fluorescence emission at a first wavelength; and a second wavelength filter configured to bandpass the fluorescence emission at a second wavelength. The second wavelength is different from the first wavelength. The system also includes a first light sensor configured to receive the fluorescence emission at the first wavelength. The system also includes a second light sensor configured to receive the fluorescence emission at the second wavelength; and a controller configured to receive first output data from the first light sensor and second output data from the second light sensor.

In one aspect, the source of light is a light emitting diode (LED).

In one aspect, the extracellular pH level is determined over a layer of bacteria developed on a tooth plaque, in drinking water, or over a surface of a plant.

DESCRIPTION OF THE DRAWINGS

The foregoing aspects and many of the attendant advantages of the inventive technology will become more readily appreciated as the same are understood with reference to the following detailed description, when taken in conjunction with the accompanying drawings, wherein.

DETAILED DESCRIPTION

While several embodiments have been illustrated and described, it will be appreciated that various changes can be made therein without departing from the spirit and scope of the claimed subject matter.

Figure 4A:
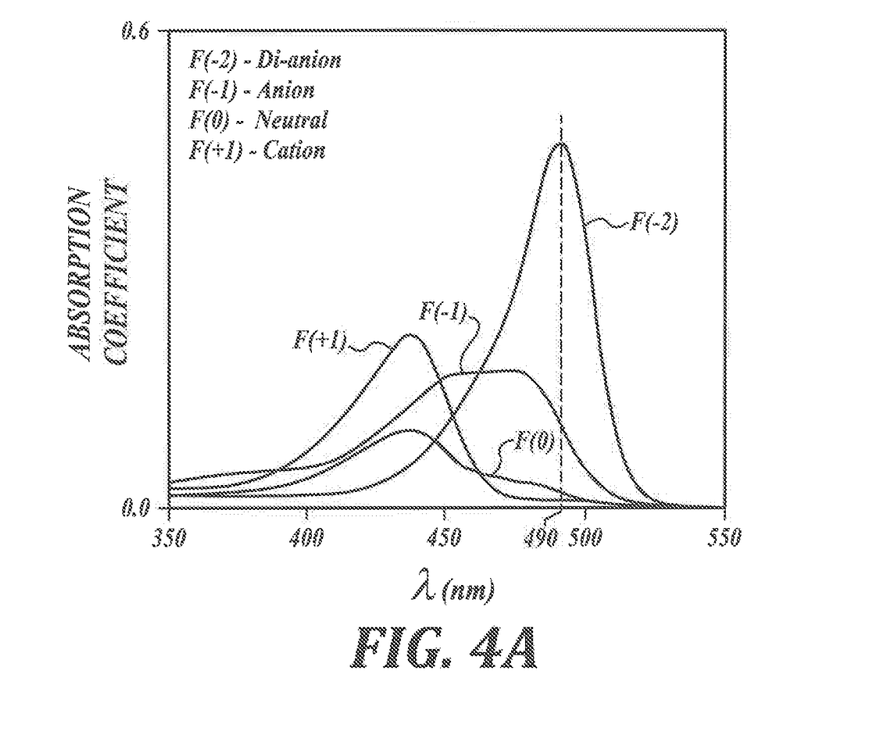
FIG. 4A is a graph of absorption coefficient for different components of fluorescein as a function of wavelength in accordance with an embodiment of the present technology.

FIG. 4A is a graph of absorption intensity for different components of fluorescein as a function of wavelength in accordance with an embodiment of the present technology. The horizontal axis of the graph shows absorption wavelengths in nanometers. The vertical axis shows the absorption coefficient for the four pH dependent components of the fluorescein: dianion, anion, neutral and cation. The dianion component has the largest absorption coefficient having an absorption peak at around 490 nm. The absorption plateau of the anion component extends from about 450 nm to about 480 nm. The neutral and cation components also absorb light within a range of wavelengths, but, as discussed with reference to FIG. 4B below, these components do not emitted fluorescent light.

Figure 4B:
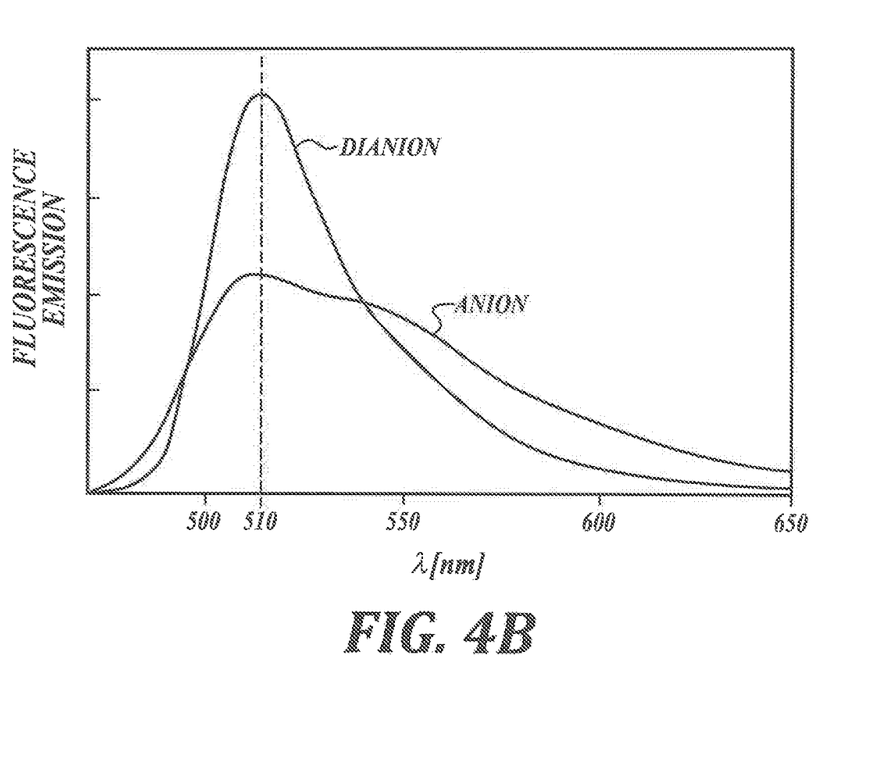
FIG. 4B is a graph of fluorescence emission of dianion and anion components of fluorescein as a function of wavelength in accordance with an embodiment of the present technology.

FIG. 4B is a graph of fluorescence emission spectral profiles of the pH dependent dianion and anion components of fluorescein as a function of wavelength in accordance with an embodiment of the present technology. The horizontal axis of the graph shows fluorescent emission wavelengths in nanometers. The vertical axis shows the fluorescent emission (e.g., in counts) for the two components of the fluorescein that fluorescence: dianion and anion. The fluorescence of the dianion component is dominant of the two, peaking at about 510 nm. The anion component exhibits more of a plateau—like fluorescence from about 505 nm to about 560 nm.

Figure 5:
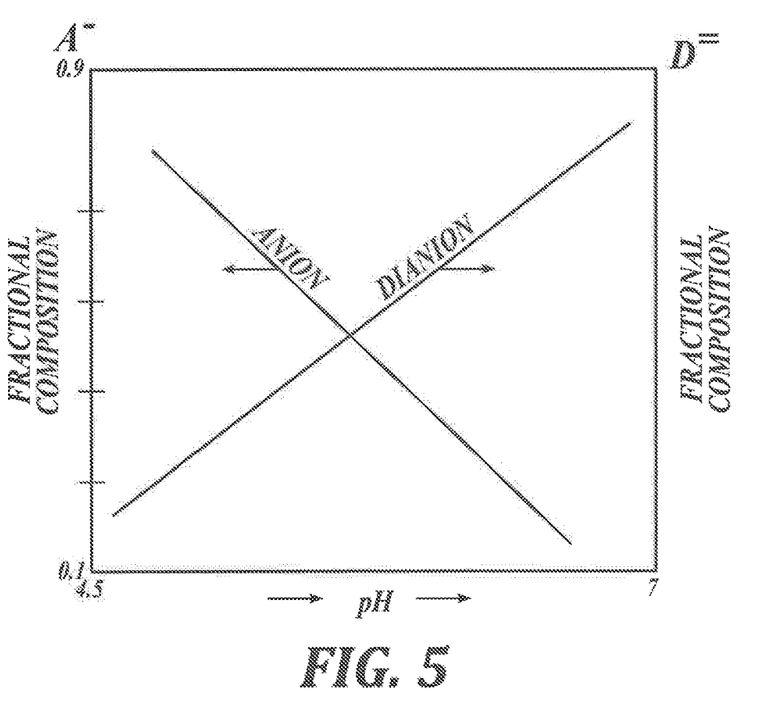
FIG. 5 is a graph showing the pH calibration based on the fluorescence as a function of pH in accordance with an embodiment of the present technology.

FIG. 5 is a graph showing the fraction of the anion phase and the dianion phase of fluorescein as a function of pH in accordance with an embodiment of the present technology. The horizontal axis shows the pH value, and the vertical axes show the relative amounts of each fluorescent fluorescein phase. The relative fraction of the anion component is shown on the left vertical axis, and the relative fraction of the dianion component is shown on the right vertical axis. As the pH increases from about 4.5 to about 7, the amount of anion component decreases and the amount of the dianion component increases. As a result, the fluorescence emissions of the anion component decrease with the increased pH, and the fluorescence emissions of the dianion component increase with the increased pH.

Figure 6:
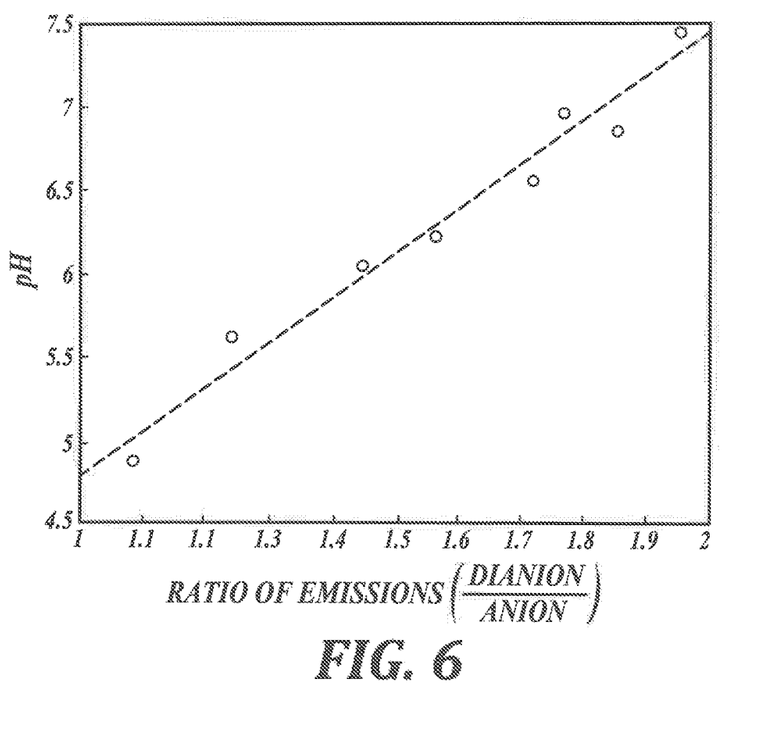
FIG. 6 is a graph showing pH values as a function of a ratio of fluorescence emission of the anion phase and the dianion phase of fluorescein in accordance with an embodiment of the present technology.

FIG. 6 is a graph showing pH values as a function of a ratio of fluorescence emission of the anion phase and the dianion phase of fluorescein in accordance with an embodiment of the present technology. The horizontal axis of the graph shows the ratio of the fluorescent emissions of the dianion component and the anion component. The vertical axis shows the pH value for a given ratio. The graph shown in FIG. 6 may be derived from the graph shown in FIG. 5 above. A given ratio of fluorescent emissions of, for example, 1.3 indicates the pH value of about 5.5. Similarly, a ratio of fluorescence emissions of 1.7 indicates the pH value of about 6.6. Therefore, if a ratio of the fluorescent emissions of the dianion component and the anion component is known, the pH value can be estimated based on the graph. Some embodiments of the method for determining the fluorescence emissions of the dianion component and the anion component are described with reference to FIG. 7 below.

Figure 7:
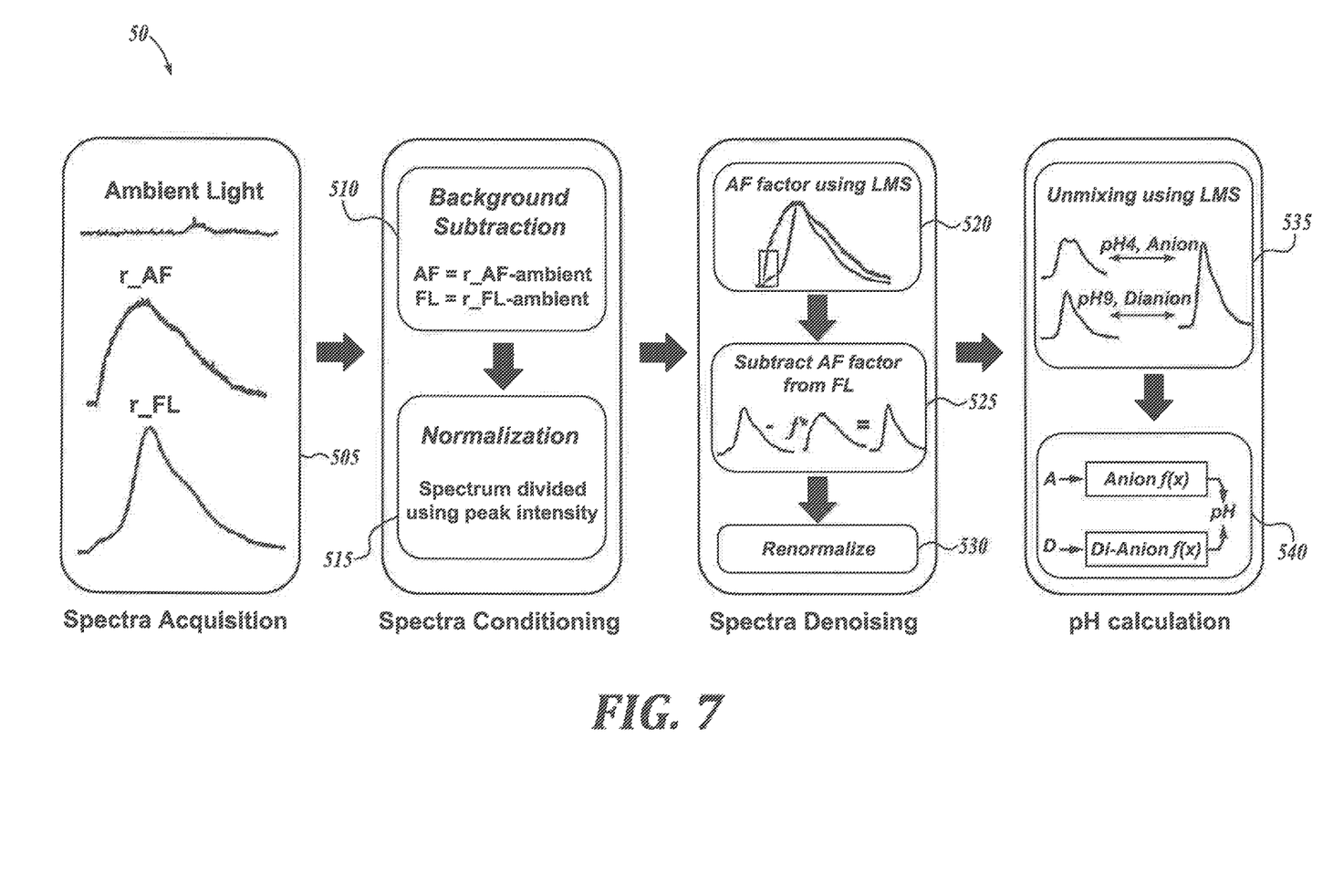
FIG. 7 is a flowchart of a method for pH measurement in accordance with an embodiment of the present technology.

FIG. 7 is a flowchart of a method 50 for calibration of the spectral data to derive the pH in accordance with an embodiment of the present technology. In some embodiments, the method may include additional steps or may be practiced without all steps illustrated in the flow chart.

In block 505, measurements are obtained of the ambient light, raw auto fluorescence (r_AF) and raw fluorescence (r_FL) spectra. In some embodiments, a blue 420 nm light emitting diode (LED) may be used as a source of the excitation light. These measurements may be performed for a range of known pH values, for example, ranging from pH 4 to 9. Multiple measurements may be performed at the same pH and then averaged.

In block 510, background subtraction is performed. For example, the auto fluorescence (AF) is determined by subtracting the ambient light spectrum from the raw auto fluorescence (r_AF) spectrum, and the fluorescence (FL) is determined by subtracting the ambient light spectrum from the raw fluorescence (r_FL). Blocks 510 and 515 may be collectively referred to as spectra conditioning.

In block 520, the auto-fluorescence is factored using the least mean square (LMS) regression to mathematically describe the auto fluorescence. In block 525, the auto fluorescence (AF) factor is subtracted from the fluorescence (FL). In block 530, the fluorescence (FL) is renormalized using the peak intensity value the spectral range. Blocks 520, 525 and 530 may be collectively referred to as a spectra denoising.

In block 535, the anion and dianion components are unmixed using least mean square (LMS) method. In some embodiments, the anion end member spectrum may be assigned at a pH value of 4 (where the fluorescence of the anion component dominates the overall fluorescence) and the dianion end member spectrum may be assigned at pH value of 9 (where the fluorescence of the dianion component dominates the overall fluorescence). As a result, two separate functions of light intensity as a function of pH are obtained, one for the anion component, and another for the dianion fractional component. In block 540, the pH value of the specimen may be determined using the obtained functions for the anion and dianion components. Blocks 535 and 540 may be collectively referred to as a pH calculation.

Figure 8A:
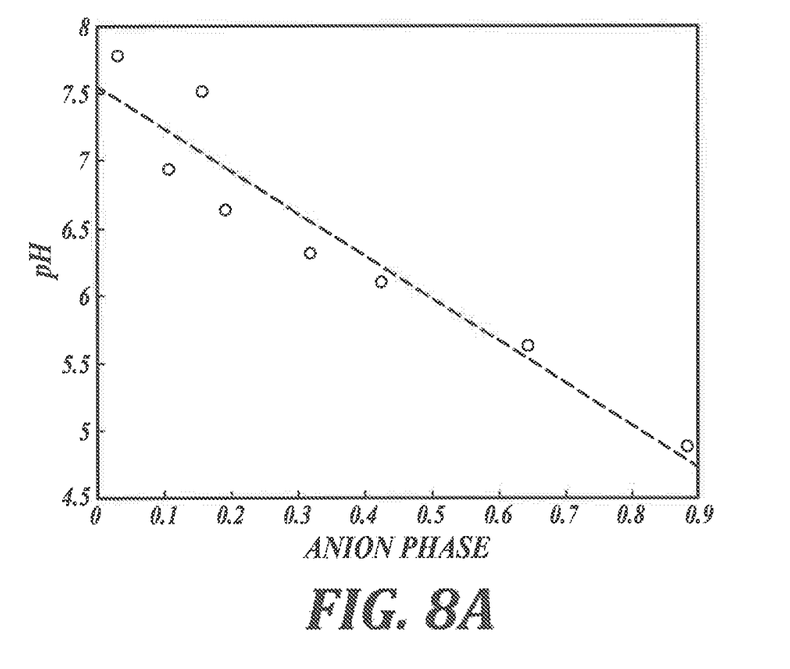
FIG. 8A is a calibration graph showing a relationship of anion component of fluorescein and pH in accordance with an embodiment of the present technology.
Figure 8B:
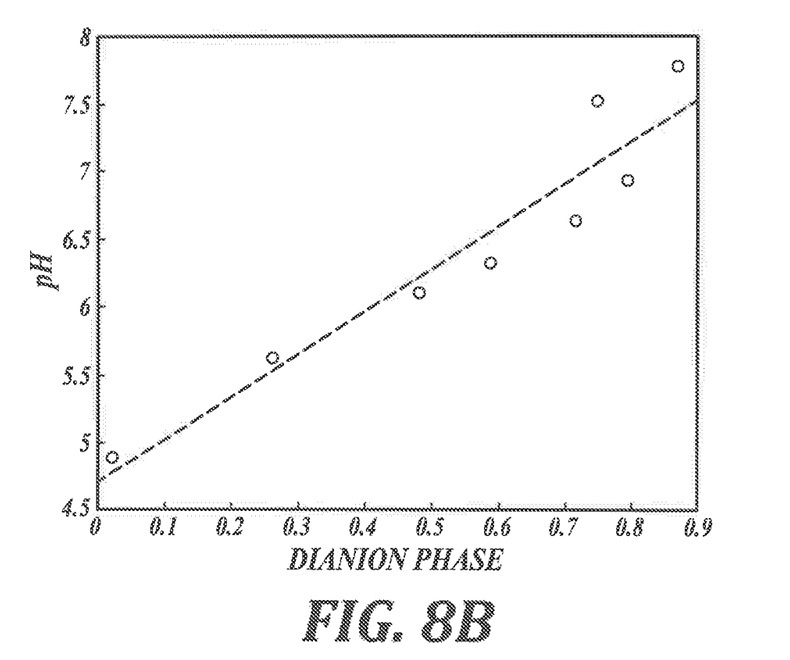
FIG. 8B is a calibration graph showing a relationship of a dianion component of fluorescein and pH in accordance with an embodiment of the present technology.

FIG. 8A is a calibration graph showing a relationship of anion phase fraction of fluorescein and its corresponding pH value, and FIG. 8B is a calibration graph showing a relationship of a dianion phase fraction of fluorescein and its corresponding pH value in accordance with embodiments of the present technology. The horizontal axis in the graphs of FIGS. 5A and 5B corresponds to the anion and dianion components (also referred to as phases). The vertical axes in both graphs correspond to the pH value.

Returning to FIG. 8A, at the pH value of about 4.5, the anion component dominates the mixture of the anion and dianion. Returning to FIG. 8B, as the pH value increases from about 4.5 to about 7.5, the dianion component starts to dominate, reaching about 90% of the combination at the pH of 7.5. For the illustrated examples, the calibration curve for the anion (A) component is:

$$pH=-2.55*A+7.156 \tag{Eq. 2}$$

with correlation $R^2=0.99$, and the calibration curve for the dianion (D) component is:

$$pH=2.613*D+4.552 \tag{Eq. 3}$$

also with correlation $R^2=0.99$.

Based on the calibration curves, the fluorescence emissions of the dianion and the anion components can be correlated back to the pH value of the biofilm as explained with reference to FIGS. 9 and 10 below.

Figure 9:
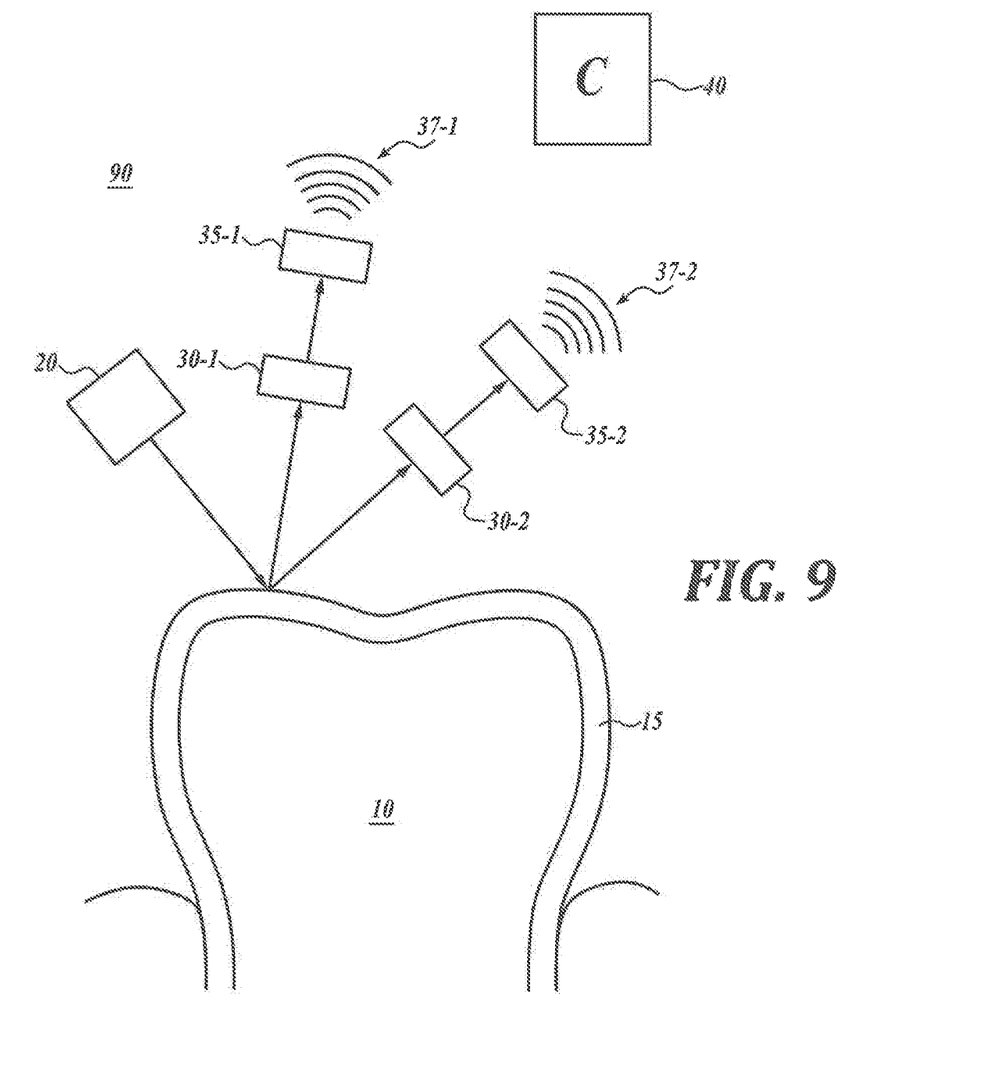
FIG. 9 is a schematic diagram of a pH measurement system in accordance with an embodiment of the present technology.

FIG. 9 is a schematic diagram of a pH measurement system 90 in accordance with an embodiment of the present technology. The system 90 may be used to determine pH value of over a layer of bacteria developed on a tooth plaque 15 over the tooth 10 or plaque over surfaces used for food processing. However, in other embodiments, the system 19 may be used to determine the pH value of other extracellular targets, for example, in drinking or irrigation water; over a surface of a plant, which may be a vegetable plant or a fruit plant; in recycled water used for washing vegetables, or over a surface of food processing equipment. In some embodiments a source of light 20 (e.g., an LED, a laser, a laser diode, a discharge lamp, etc.) emits light toward the target 15. In operation, the target 15 may be partially or completely covered by the fluorescein.

As explained above, the ratio of the fluorescent components (anion and dianion components) is a function of the pH value of the target 15. These fluorescent components emit light at their respective fluorescence spectra. The fluorescent emissions may be captured by light sensors 35-1 and 35-2. For example, a wavelength filter 30-1 may bandpass-filter fluorescent light before reaching the light sensor 35-1, and a wavelength filter 30-2 may bandpass-filter fluorescent light before reaching the light sensor 35-2. The bandpass of the wavelength filters 30-1 and 30-2 may be selected such that the wavelength filter 30-1 transmits the fluorescent light corresponding to selected wavelengths of the anion spectrum, while the wavelength filter 30-2 transmits the fluorescent light corresponding to selected wavelengths of the anion spectrum. As a result, the light sensors 35-2 and 35-2 (e.g., photodiodes) capture the light intensity of the anion and dianion components of the fluorescent light. In some embodiments, the excitation wavelength emitted by the source of light 20 may be within a range of 404-430 nm, for example 420 nm. In some embodiments, the fluorescence wavelength of the dianion component may be within a range of 515 to 525 nm. In some embodiments, the fluorescence wavelength of the anion component may be within a range of 545 to 555 nm. The above numerical values are non-exclusive, and other values are also possible.

The light intensities of the fluorescent light that are captured by the light sensors 35 may be transferred to a controller 40. In some embodiments, data transmission 37 may be wireless. In other embodiments, data from the light sensors 35 may be transferred to the controller 40 through wires.

Figure 10:
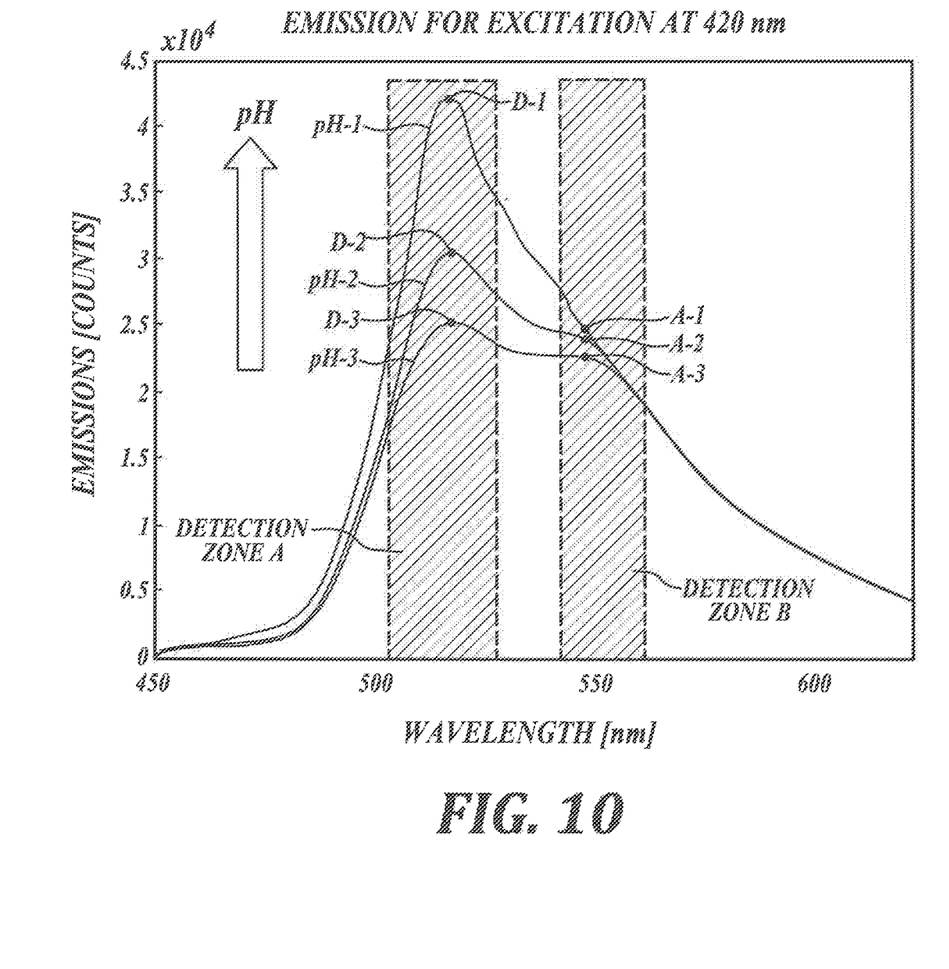
FIG. 10 is a graph showing pH-dependent fluorescence emission spectral profile of a combined anion and dianion components of fluorescein as a function wavelength in accordance with an embodiment of the present technology.

FIG. 10 is a graph showing pH-dependent fluorescein fluorescence spectral profile which consists of a combined anion and dianion components of fluorescein as a function of wavelength in accordance with an embodiment of the present technology. The horizontal axis represents the wavelength of fluorescence emission in nanometers. The vertical axis represents the intensity of the fluorescent emission in counts. The excitation light source is a 420 nm (peak) LED. Curves shown in the graph correspond to the increasing pH level from pH-3 to pH-1. A detection zone A corresponds to the wavelength band for the dianion fluorescent emissions, and the detection zone B corresponds to the wavelength band for the anion fluorescent emissions. In operation, the illustrated wavelength bands may be implemented using appropriate wavelength bandpass filters 30.

When, for example, the light sensor 35-1 measures fluorescent emission D-2 within the detection zone A (dianion) and the light sensor 35-2 measures fluorescent emission A-2 within the detection zone B (anion), such measurements indicate the pH level of the specimen being pH-2. As another example, when the light sensor 35-1 measures fluorescent emission D-1 within the detection zone A (dianion) and the light sensor 35-2 measures fluorescent emission A-1 within the detection zone B (anion), such measurements indicate the pH level of the specimen being pH-1. These pH levels may be obtained a priori from the calibration described with reference to FIG. 7, as shown as Equations (1) and (2) with reference to FIGS. 8A and 8B.

In some embodiments, the determination of the pH level may be generalized as:

$$\text{Measured Spectrum} = A_1 * (\text{Anion Spectrum}) + A_2 * (\text{Dianion Spectrum})$$

where $A_1$ and $A_2$ are calibration constants.

Generally, pH depends on a ratio of the spectral intensities of the anion and dianion components. At relatively high pH (e.g., pH of 7.5) the ratio reaches its maximum. At low pH (e.g., pH of 4) the ratio reaches its minimum. In between these extremes the pH is derivable from the calibration curve shown in FIG. 6.

Many embodiments of the technology described above may take the form of computer- or controller-executable instructions, including routines executed by a programmable computer or controller. Those skilled in the relevant art will appreciate that the technology can be practiced on computer/controller systems other than those shown and described above. The technology can be embodied in a special-purpose computer, controller or data processor that is specifically programmed, configured or constructed to perform one or more of the computer-executable instructions described above. Accordingly, the terms "computer" and "controller" as generally used herein refer to any data processor and can include Internet appliances and hand-held devices (including palm-top computers, wearable computers, cellular or mobile phones, multi-processor systems, processor-based or programmable consumer electronics, network computers, mini computers and the like).

The present application may also reference quantities and numbers. Unless specifically stated, such quantities and numbers are not to be considered restrictive, but exemplary of the possible quantities or numbers associated with the present application. Also in this regard, the present application may use the term "plurality" to reference a quantity or number. In this regard, the term "plurality" is meant to be any number that is more than one, for example, two, three, four, five, etc. The terms "about," "approximately," etc., mean plus or minus 5% of the stated value.

From the foregoing, it will be appreciated that specific embodiments of the technology have been described herein for purposes of illustration, but that various modifications may be made without deviating from the disclosure. Moreover, while various advantages and features associated with certain embodiments have been described above in the context of those embodiments, other embodiments may also exhibit such advantages and/or features, and not all embodiments need necessarily exhibit such advantages and/or features to fall within the scope of the technology. Accordingly, the disclosure can encompass other embodiments not expressly shown or described herein.

What is claimed is:

1. A method of measuring an extracellular pH level using multiple wavelengths emitted by a fluorescent substance, the method comprising:
   exciting the fluorescent substance at an excitation wavelength;
   measuring a first fluorescence intensity at a first wavelength of a fluorescence emission;
   measuring a second fluorescence intensity at a second wavelength of the fluorescence emission, wherein the second wavelength is different from the first wavelength; and
   determining the extracellular pH level based on the first fluorescence intensity at the first wavelength and the second fluorescence intensity at the second wavelength,
   wherein the fluorescent substance is a fluorescein, and
   wherein the method further comprises:
   calibrating the fluorescence emission of an anion component and a dianion component of the fluorescein by:
   subtracting ambient emission from the anion component and the dianion component; and
   dividing the anion component and the dianion component by a peak spectral intensity to normalize the anion component and the dianion component.

2. A method of measuring an extracellular pH level using multiple wavelengths emitted by a fluorescent substance, the method comprising:
   exciting the fluorescent substance at an excitation wavelength;
   measuring a first fluorescence intensity at a first wavelength of a fluorescence emission;
   measuring a second fluorescence intensity at a second wavelength of the fluorescence emission, wherein the second wavelength is different from the first wavelength; and
   determining the extracellular pH level based on the first fluorescence intensity at the first wavelength and the second fluorescence intensity at the second wavelength,
   wherein the fluorescent substance is a fluorescein;
   wherein the extracellular pH level is determined based on:

$$\text{Measured Spectrum} = A1 * (\text{Anion Spectrum}) + A2 * (\text{Dianion Spectrum})$$

where:
   A1 and A2 are calibration constants,
   Dianion Spectrum is measured at the first wavelength, and
   Anion Spectrum is measured at the second wavelength.

3. The method of claim 2, wherein the excitation wavelength is within a range of 404-430 nm.

4. The method of claim 3, wherein the excitation wavelength is 420 nm.

5. The method of claim 2, wherein the first fluorescence wavelength is within a range of 515 to 525 nm.

6. The method of claim 2, wherein the second fluorescence wavelength is within a range of 545 to 555 nm.

7. The method of claim 2, wherein the extracellular pH level is determined over a layer of bacteria developed on a tooth plaque or over surfaces used in food processing.

8. The method of claim 2, wherein the extracellular pH level is determined in drinking water, irrigation water, or water recycled from washing vegetables.

9. The method of claim 2, wherein the extracellular pH level is determined over a surface of a plant.

10. The method of claim 9, wherein the plant is a vegetable plant.

11. A system for measuring an extracellular pH level using multiple wavelengths emitted by a fluorescent substance, the system comprising:
- a source of light configured to emit excitation light toward a target biological surface that includes the fluorescent substance;
- a first wavelength filter configured to bandpass a fluorescence emission at a first wavelength;
- a second wavelength filter configured to bandpass the fluorescence emission at a second wavelength, wherein the second wavelength is different from the first wavelength;
- a first light sensor configured to receive the fluorescence emission at the first wavelength;
- a second light sensor configured to receive the fluorescence emission at the second wavelength; and
- a controller configured to receive first output data from the first light sensor and second output data from the second light sensor, wherein the controller is further configured to determine the extracellular pH level based on:

$$\text{Measured Spectrum} = A1*(\text{Anion Spectrum}) + A2*(\text{Dianion Spectrum})$$

where:
A1 and A2 are calibration constants,
Dianion Spectrum is measured at the first wavelength, and
Anion Spectrum is measured at the second wavelength.

12. The system of claim 11, wherein the excitation wavelength is within a range of 404-430 nm.

13. The system of claim 12, wherein the excitation wavelength is 420 nm.

14. The system of claim 11, wherein the first fluorescence wavelength is within a range of 515 to 525 nm.

15. The system of claim 11, wherein the second fluorescence wavelength is within a range of 545 to 555 nm.

16. The system of claim 11, wherein the extracellular pH level is determined over a layer of bacteria developed on a tooth plaque, in drinking water, or over a surface of a plant.

17. A method of measuring an extracellular pH level using multiple wavelengths emitted by a single fluorescent substance, the method comprising:
- exciting the fluorescent substance at an excitation wavelength;
- measuring a first fluorescence intensity at a first wavelength of a fluorescence emission, wherein the first fluorescence intensity has a first correlation with the extracellular pH level;
- measuring a second fluorescence intensity at a second wavelength of the fluorescence emission, wherein the second wavelength is different from the first wavelength,
  - wherein the second fluorescence intensity has a second correlation with the extracellular pH level, and
  - wherein one of the first correlation and the second correlation is positive and
  - another of the first correlation and the second correlation is negative; and
- determining the extracellular pH level based on the first fluorescence intensity at the first wavelength and the second fluorescence intensity at the second wavelength.

18. The method of claim 17, wherein the extracellular pH level is determined based on:

$$\text{Measured Spectrum} = A1*(\text{Anion Spectrum}) + A2*(\text{Dianion Spectrum})$$

where:
A1 and A2 are calibration constants,
Dianion Spectrum is measured at the first wavelength, and
Anion Spectrum is measured at the second wavelength.

* * * * *

UNITED STATES PATENT AND TRADEMARK OFFICE
CERTIFICATE OF CORRECTION

PATENT NO. : 12,241,901 B2
APPLICATION NO. : 17/260957
DATED : March 4, 2025
INVENTOR(S) : Eric J. Seibel et al.

It is certified that error appears in the above-identified patent and that said Letters Patent is hereby corrected as shown below:

On the Title Page

| Column | Line(s) | |
|---|---|---|
| 1 | 1 | item (73), under "Assignee", delete "The University" and insert -- University -- |

In the Claims

| Column | Line(s) | |
|---|---|---|
| 12 | 23-24 | Claim 17, delete "another of the first correlation and the second correlation is negative; and" and insert the same at Line 22, after "is positive and", as a continuation sub point |

Signed and Sealed this
Twenty-seventh Day of January, 2026

John A. Squires
*Director of the United States Patent and Trademark Office*